(12) United States Patent
Carbone et al.

(10) Patent No.: US 7,118,764 B2
(45) Date of Patent: Oct. 10, 2006

(54) PROCESS FOR COOKING/DRYING HIGH-AMYLOSE STARCHES

(75) Inventors: Domenico Carbone, Pasturana (IT); Claude Quettier, Erquinghem Lys (FR); Giovanni Semino, Spinola (IT); Ernesto Fossati, Novi Ligure (IT)

(73) Assignee: Roquette Freres, Lestrem (FR)

( * ) Notice: Subject to any disclaimer, the term of this patent is extended or adjusted under 35 U.S.C. 154(b) by 534 days.

(21) Appl. No.: 10/105,661

(22) Filed: Mar. 25, 2002

(65) Prior Publication Data

US 2003/0029444 A1 Feb. 13, 2003

(30) Foreign Application Priority Data

Mar. 26, 2001 (FR) .................................. 01 04023

(51) Int. Cl.
*A61K 9/14* (2006.01)
*F26B 3/08* (2006.01)
*F26B 5/04* (2006.01)

(52) U.S. Cl. .......................... 424/489; 34/372; 34/413; 424/401; 426/578

(58) Field of Classification Search ................ 424/489, 424/49, 401, 48, 451, 452, 456; 426/578, 426/660, 661; 34/372, 413
See application file for complete search history.

(56) References Cited

U.S. PATENT DOCUMENTS 3,086,890 A 4/1963 Sarko
3,607,394 A 9/1971 Germino
3,765,917 A * 10/1973 Hijiya et al. ............. 106/145.5
4,515,769 A * 5/1985 Merritt et al. ................ 424/49
5,888,548 A * 3/1999 Wongsuragrai et al. ..... 424/489

FOREIGN PATENT DOCUMENTS

EP 0 366 898 A 5/1990
WO 99 09066 A 2/1999
WO WO 9909066 A1 * 2/1999

* cited by examiner

*Primary Examiner*—Michael G. Hartley
*Assistant Examiner*—Micah-Paul Young
(74) *Attorney, Agent, or Firm*—Young & Thompson

(57) ABSTRACT

The subject of the present invention is a process for preparing pregelatinized high amylose starch, comprising the steps consisting of:
  forming a suspension comprising a high amylose starch and water;
  subjecting the said suspension to steam jet cooking at a temperature of between 125 and 135° C. so as to obtain a pregelatinized high amylose starch paste;
  cooking and drying the said pregelatinized starch paste on a drum dryer at a pressure of between 2 and 10 bar, so as to obtain a pregelatinized high amylose starch.

Its subject is also a pregelatinized high amylose starch, having an apparent density of less than 0.4 g/ml for a mean particle size of 100 micrometers. Its subject is in addition the use of such a starch for the manufacture of soft gelatin capsules or of hard gelatin capsules and the film-coating of pharmaceutical, dietary or agricultural solid forms.

10 Claims, No Drawings of the patent invention is a novel process for preparing pregelatinized high-amylose starches.

PROCESS FOR COOKING/DRYING HIGH-AMYLOSE STARCHES

FIELD OF THE INVENTION

The subject of the invention is a novel process for preparing pregelatinized high-amylose starches.

Its subject is also the starches obtained by this process.

BACKGROUND OF THE INVENTION

Pregelatinized starches are generally prepared by thermal, chemical or mechanical techniques which can cause swelling of the starch granules so that they are soluble in cold water.

The preferred techniques are spray-drying, cooking on a drum or extrusion. Autoclaving or indirect heating on a heat exchanger are cooking processes which tend to produce complex colloidal dispersions consisting of intact, fragmented and swollen granules.

It is well known that high amylose starches, that is to say which have more than 50% by weight of amylose, are particularly difficult to disperse and require high cooking temperatures.

The document U.S. Pat. No. 3,086,890 describes a process for preparing pregelatinized amylose. This process consists in autoclaving at 191° C., under pressure, a solution of amylose containing at most 25% by weight of dry matter, and then drum-drying at 110–200° C. The powders obtained are amorphous and form irreversible gels after dispersion. Their apparent density is high, that is to say generally greater than 0.4 g/ml.

The document U.S. Pat. No. 3,607,394 describes a process for the pregelatinization of starches having amylose contents of less than 60% by weight. This process consists in cooking the starch at 149° C., followed by drum-drying, spray-drying or another type of drying means.

The document EP 0 366 898 describes a coupled cooking/spray-drying process which makes it possible to obtain amorphous products, which are practically free of retrogradation, and which have an apparent density greater than that of an identical starch which has been subjected to the same process but in two separate stages, that is an apparent density greater than 0.45 g/ml. The cooking of high amylose starches is carried out on a jet cooker at 143° C. and the spray-drying is carried out with an inlet air temperature of 220° C. This document presents, in FIG. 7, a comparison of various prior art pregelatinized starches.

Starting from this teaching, the applicants have now found, after long research studies, that it was possible to prepare a pregelatinized high amylose starch using a particular process leading to products of low apparent density while working at not very high temperatures, which none of the prior art techniques made it possible to obtain.

OBJECTS AND DETAILED DESCRIPTION OF THE INVENTION

The subject of the invention is therefore a process for preparing pregelatinized high amylose starch, characterized in that it comprises the steps consisting of:

forming a suspension comprising a high amylose starch and water;

subjecting the said suspension to steam jet cooking at a temperature of between 125 and 135° C. so as to obtain a pregelatinized high amylose starch paste;

drying the said pregelatinized starch on a drum dryer at a pressure of between 2 and 10 bar, so as to obtain a pregelatinized high amylose starch.

The pregelatinized high amylose starch obtained may then be recovered and ground so as to obtain a powder having a particle size which is chosen according to the uses which will be subsequently made thereof.

The expression high amylose starches for the purposes of the present invention denotes starches having an amylose content greater than or equal to 50% by weight, and preferably of between 50 and 80% by weight, obtained from any plant origin, such as in particular maize, potato, cassava.

Preferably, the process according to the invention uses a maize starch such as, for example, EURYLON® marketed by the Assignee.

The invention also applies to chemically or physically modified high amylose starches. Preferably, the modified starch will be chosen from the group consisting of acetylated, hydroxypropylated, carboxy-methylated and fluidified starches, and starch octenyl succinates.

According to a preferred variant of the process according to the invention, an acetylated starch will be chosen.

The starch suspension is prepared at a dry matter content of between 30 and 40% by weight so as to obtain a suspension in water.

This suspension is then pregelatinized using a tuyere at the outlet of which a steam counter-pressure is applied which is sufficient to reach a cooking temperature for the suspension of between 125 and 135° C. while maintaining an acceptable viscosity so that the flow rate of the milk coming out after cooking is not too low. For example, a counter-pressure of the order of 2 to 3 bar will be applied.

Surprisingly and unexpectedly, this cooking temperature is necessary and sufficient to obtain good pregelatinized starch solubility. The amylose fraction exists, according to the process in accordance with the invention, in amorphous form, whereas the prior art processes for cooking high amylose starches lead to an amylose which has a high tendency to undergo retro-gradation.

The expression tuyere is understood to mean any direct steam jet cooking device allowing instant cooking of a starch suspension using pressurized steam.

A pregelatinized starch paste is obtained after this cooking, which is then dried on a drum dryer.

Such an equipment makes it possible to reproduce, on one and the same device, the cooking and drying stages by exploiting the heat transferred from the surface of the drums heated with steam to the starch paste. Steam pressure values of the order of 2 to 10 bar will be applied, for example, according to the type of starch used. The starch paste is uniformly spread in a thin film over the hot surface of the drums by applying components. The drums are driven in rotation, at a speed of the order of 5 to 8 revolutions per minute. Thus, the cooking of the paste is continued, followed by drying. The film formed is then scraped using a scraping blade so as to detach a sheet which can then be ground.

The process according to the invention makes it possible to homogeneously obtain pregelatinized high amylose starches without the need for the use of very high temperatures as taught by the prior art. The process according to the invention is particularly advantageous because it uses simple techniques, with a lower energy cost than the known techniques of spray-drying or autoclaving.

The pregelatinized high amylose starches according to the invention are characterized by an apparent density of less than 0.4 g/ml for a mean particle size of 100 micrometers, which is particularly surprising given the higher densities obtained according to the prior art techniques and in particular those described in patent EP-B1 0 366 898.

Their solubility in lukewarm water is good, in the region of 80%, whereas it is less than 30% when the tuyere cooking stage is eliminated.

These starches have, in addition, various applicative advantages such as, in particular, a good compression capacity, and in particular very good capacities to form a film. This capacity is particularly advantageous for film coating tablets in particular, but also for numerous other applications requiring the formation of a barrier to moisture and to air. To the knowledge of the applicants, such pregelatinized high amylose starches capable of having film-forming properties did not exist on the market. The subject of the invention is therefore, in addition, the use of pregelatinized high amylose starches for the manufacture of soft gelatin capsules or of hard gelatin capsules, as well as for the coating of solid forms in pharmacy, human foods, animal foods, agrochemistry or plant substances such as seeds.

The subject of the invention is also the use of high amylose starches obtained according to the invention for the preparation of freshening films, also called flavour sheets. These flavour sheets are small squares of edible films, which are very fine, highly flavoured, and used as breath fresheners by dissolving rapidly in the buccal cavity. The applicants have observed that in addition to the remarkable film-forming properties of the starches according to the invention, the latter had an advantageous capacity to encapsulate molecules with low solubility in water, such as flavourings or certain active ingredients. Indeed, during the formulation of such films based on film-forming polymers, when about 5% of flavouring or of active ingredient which are weakly soluble in water are added to the film-forming preparation, a total phase separation occurs during the spreading of the film, between the hydrophobic molecules and the other components. The film-forming solution is pushed to the sides of the band of film, whereas the centre is only composed of flavouring or of active ingredient. The film obtained therefore does not constitute a homogeneous thin layer. The addition, before incorporation of the flavouring, of a pregelatinized high amylose starch according to the invention allows, surprisingly and unexpectedly, inclusion of the flavourings or active ingredients which are weakly soluble in water, on the one hand, and an excellent film quality, on the other hand. Without wishing to be bound to any theory, the applicants are of the opinion that this encapsulation property is linked to the amorphous state of the precooked amylose according to the process in accordance with the invention, given that the precooked high amylose starches according to the prior art processes do not possess this encapsulation property. The film obtained has the desired properties, namely good solubility, adequate mechanical properties, strong flavouring and no adherence between each film during packaging.

Thus, an edible film which is highly flavoured or which comprises an active ingredient which is weakly soluble in water, characterized in that it comprises a pregelatinized high amylose starch according to the invention, constitutes, to the knowledge of the applicants, a novel industrial product. The expression "weakly soluble in water" is understood to mean, according to the present invention, flavourings or active ingredients which have a solubility in water of less than 5% by weight.

According to a preferred embodiment of the film according to the invention, the latter comprises, on a dry matter basis, 5 to 40%, preferably 5 to 25%, of pregelatinized high amylose starch according to the invention. According to a still more preferred embodiment of the invention, the said pregelatinized high amylose starch is stabilized, for example, by acetylation or hydroxypropylation.

The film comprises, in addition, any other film-forming polymer commonly used in practice, such as in particular high amylopectin starches, modified or otherwise, high amylose starches, modified or otherwise, standard or special maltodextrins, film-forming polysaccharides and proteins such as gelatin, pullulan, plant gums, gluten.

According to a preferred variant, the edible film comprises 5 to 40% of pregelatinized high amylose starch according to the invention and 40 to 80% of high amylopectin starch. The balance for 100% consists of flavourings, active ingredients, sweeteners, one or more humectants and optionally colourings. The final water content of the films according to the invention is generally about 12%.

The expression high amylopectin starch is understood to mean the so-called waxy starches, derived in particular from maize or potato.

According to a still more preferred variant, the said film comprises, on a dry matter basis, 5 to 40%, preferably 5 to 25%, of pregelatinized high amylose starch according to the invention, and 40 to 80%, preferably 40 to 70%, of waxy starch fluidified by the acid route.

A waxy starch derived from maize fluidified by techniques known to persons skilled in the art would be preferably chosen.

Of course, the film according to the invention may be used as it is as a flavour sheet for freshening the breath, but it may also be used for the film-coating of various supports, in particular dietary or pharmaceutical supports. There may be mentioned, without limitation, the film-coating of tablets, confectioneries, or any other support.

The advantageous properties of encapsulation of substances weakly soluble in water of the starches according to the invention may also be exploited in any other type of application requiring such properties, in aqueous medium or in the dry state.

The invention will be understood more clearly on reading the following examples, which are intended to be explanatory and nonlimiting.

EXAMPLES

Example 1

High amylose starches, modified or otherwise, are prepared according to a process comprising the following steps:
preparation of a suspension of starch and water
cooking in a tuyere
drying on a drum dryer
recovery of a powder In all cases, the initial starch is EURYLON®7 marketed by the Assignee, having an amylose content of 70% by weight.

The various process parameters are presented in Table 1, as well as the apparent densities and the mean particle sizes of the various products obtained. The apparent density is measured according to the pharmaceutical technical method 2.9.16 of the European Pharmacopoeia, 3rd edition. The mean particle size is calculated from the particle size measured by sieving on successive sieves of 500, 315, 200, 150, 100 and 50 micrometers.

The displacement density is measured according to the method described in patent EP-B1 0 366 898.

|  | TRIAL 1 EURYLON®7 | TRIAL 2 EURYLON®7 ACETYL | TRIAL 3 EURYLON®7 ACETYL | TRIAL 4 EURYLON®7 OCTENYL SUCCINATE | TRIAL 5 EURYLON®7 HYDROXYPROPYL | TRIAL 6 EURYLON®7 FLUIDIFIED ACIDIC |
|---|---|---|---|---|---|---|
| DRY MATTER (%) | 33.5 | 33.4 | 33.4 | 38 | 35.4 | 39 |
| TUYERE TEMPERATURE (° C.) | 130 | 135 | 135 | 133 | 135 | 135 |
| TUYERE COUNTERPRESSURE (Bar) | 2.67 | 3.1 | 3.1 | 2.92 | 3.1 | 3.1 |
| DRUM ROTATION SPEED (revolutions/min) | 6.5 | 7 | 8 | 6.5 | 7 | 6.5 |
| DRUM PRESSURE (Bar) | 10 | 10 | 2 | 10 | 10 | 10 |
| MEAN PARTICLE SIZE (µm) | 88.2 | 101.2 | 100.8 | 100.6 | 100.6 | 100.4 |
| APPARENT DENSITY (g/ml) | 0.31 | 0.22 | 0.23 | 0.34 | 0.16 | 0.37 |
| DISPLACEMENT DENSITY (g/ml) | 1.26 | 1.26 | 1.2 | 1.6 | 1.05 | 1.95 |

Example 2

In order to illustrate the film-forming properties, the product obtained according to trial No. 3 of the preceding example is solubilized in hot water (70–80° C.), with mechanical stirring, at 15% of dry matter.

The Brookfield viscosity is 4 000 mPa s at 70° C. and 5 000 mPas s at 60° C.

This solution is placed on a polyethylene support over a thickness of 45.7 micrometers.

The solution thus deposited is dried at room temperature, and gives a rigid film, which is nonbrittle, and which is insoluble in water.

This film can give rise to very numerous applications, since it can serve to coat all types of solid forms which it is desired to protect, whether they are pharmaceutical (tablets, gelatin capsules), dietary (fries, tart bases, confectioneries) or agricultural (seeds, granules).

These film-forming properties may also be applied in the manufacture of soft gelatin capsules or hard gelatin capsules.

Example 3

Flavour sheets are prepared according to the following procedure:

Formula

|  | Composition of the suspension (%) | Quantity used (g) | Composition of the film on a dry basis (%) |
|---|---|---|---|
| Fluidified waxy starch (CLEARGUM®CB90) | 27.75 | 138.75 | 55.5 |
| High amylose starch according to trial 2 example 1 | 4.60 | 23.00 | 9.2 |
| Mint flavour SILESIA | 2.50 | 12.50 | 5.0 |
| Glycerol | 15.0 | 75.0 | 30.0 |
| Sodium saccharinate | 0.15 | 0.75 | 0.3 |
| Water | 50.0 | 250.0 | — |
| Total | 100 | 500 | 100 |

In a jacketed stainless-steel bowl, disperse the CLEARGUM® in water, the glycerol and the saccharinate. Heat to 90° C.

Pour into the bowl of a KENWOOD mixer, add the pregelatinized high amylose starch and the flavouring. Mix for 1 minute at the minimum speed (solution S).

Pour the solution S into the stainless-steel bowl and heat to 85° C., degas the mixture as much as possible.

When the mixture is at 85° C., form a film on a plastic plate (thickness of paste=1.5 mm) with an automatic film applicator (bar-coater B-2105, RK printcoat) equipped with a scale preheated to 60° C.

Allow to dry in an oven at 20° C. and 80% relative humidity for 2 days and then end the drying at 20° C. under an uncontrolled atmosphere.

The film thus obtained, which is highly flavoured, is very soluble, supple and flexible, nonbrittle and not cracked, regular and homogeneous as regards the distribution of the flavour, transparent. It does not stick on contact with other films during prolonged storage. It can therefore be easily used as freshening flavour sheet, or in order to wrap or coat any type of support, in particular a dietary or pharmaceutical support.

A film prepared in the same manner but without incorporating starch according to the invention is completely heterogeneous in its centre and impossible to detach from its support in the form of a uniform sheet.

The invention claimed is:

1. A process for preparing pregelatinized high amylose starch, comprising the steps consisting of:
    forming a suspension comprising a high amylose starch and water;
    subjecting the said suspension to steam jet cooking at a temperature of between 125° C. and 135° C. so as to obtain a pregelatinized high amylose starch paste;
    drying the said pregelatinized starch paste on a drum dryer at a pressure of between 2 bar and 10 bar, so as to obtain a pregelatinized high amylose starch.

2. The process of claim 1, comprising, in addition, a step of grinding pregelatinized high amylose starch, so as to obtain a powder.

3. The process of claim 1, wherein the amylose content of the said starch is greater than or equal to 50% by weight.

4. The process of claim 3, wherein the amylose content is between 50% and 80% by weight.

5. The process of claim 1, wherein the said starch is a maize starch.

6. The process of claim 1, wherein the said suspension has a dry matter content greater than 25% by weight.

7. The process of claim 6, wherein the said suspension has a dry matter content of between 30% and 40% by weight.

8. The process of claim 1, wherein the said high amylose starch is chemically or physically modified.

9. The process of claim 8, wherein the said modified starch is selected from the group consisting of acetylated, hydroxypropylated, carboxymethylated and fluidified starches, and starch octenyl succinates.

10. The process of claim 8, wherein the said modified starch is an acetylated starch.

* * * * *